United States Patent [19]
Amirsakis

[11] 4,034,760
[45] July 12, 1977

[54] SELF CONTAINED DISPOSABLE DIAPER

[76] Inventor: Filitsa Amirsakis, 710 St. Andrews Lane, Crystal Lake, Ill. 60014

[21] Appl. No.: 668,065

[22] Filed: Mar. 18, 1976

[51] Int. Cl.² ........................................ A61F 13/16
[52] U.S. Cl. ................................ 128/287; 128/284
[58] Field of Search ............. 128/296, 290 R, 284, 128/287, 156; 206/440; 119/1

[56] References Cited
U.S. PATENT DOCUMENTS

| | | | |
|---|---|---|---|
| 3,035,578 | 5/1962 | Elmore | 128/290 R |
| 3,230,956 | 1/1966 | Kargul | 128/290 R |
| 3,274,999 | 9/1966 | Robinson | 128/156 |
| 3,369,545 | 2/1968 | Wanberg | 128/287 |
| 3,604,423 | 9/1971 | Fraser | 128/290 R |
| 3,626,900 | 12/1971 | Failla | 119/1 |
| 3,877,432 | 4/1975 | Gellert | 128/287 |
| 3,920,019 | 11/1975 | Schaar | 128/287 |
| 3,927,674 | 12/1975 | Schaar | 128/287 |

*Primary Examiner*—Aldrich F. Medbery

[57] ABSTRACT

A combined disposable diaper and disposal bag wherein a thin plastic sheet is affixed over the waterproof side of a conventional disposable diaper and sealed to it along a portion of its periphery to form a permanently attached waterproof pocket with part of the sheet that can be turned inside out to form a bag for the used disposable diaper and to form a flap with the remainder of the sheet which can be closed over the bag opening to seal the bag.

1 Claim, 4 Drawing Figures

SELF CONTAINED DISPOSABLE DIAPER

BACKGROUND OF THE INVENTION

The present invention relates to a disposable diaper and more particularly to diapers with integral disposal wrappings.

Disposable diapers, as presently designed and used, provide a convenient, inexpensive and work-saving sanitary appliance for infant care. When used in the home, solid waste contained in the diaper may be deposited in a toilet and the soilded diaper may be stored in a suitably deodorized hamper awaiting regular rubbish removal. The disposable diaper is also well suited to the current life style which encourages maximum mobility to mother and infant soon after the infant is born. Fresh supplies of disposable diapers are readily portable, need no special containers and are widely available so that it is now much more convenient to travel even long distances by a variety of modes of travel with an infant. However, the disposal of the solid disposable diaper still presents a problem. Toilets for the disposal of solid waste and proper containers for the disposal of the diaper are not readily available while traveling. The difficulty of carrying a suitable hamper for storing the soiled diaper, until it can be properly disposed of is inconvenient and in some cases nearly impossible. There is a need for a simple, effective and sanitary means for disposing of soiled disposable diapers so that they can be stored conveniently until they can be properly disposed of or left in ordinary rubbish collection containers.

SUMMARY OF THE INVENTION

The present invention solves the problem of disposing of disposable diapers by converting the diapers into its own sanitary container in which waste and the diaper itself may be enclosed and sealed. The used diaper of the present invention may be disposed of in any ordinary waste container inside the home or it may be carried in the mother's handbag while traveling, visiting friends or enjoying the out-of-doors.

The invention may embody a plastic bag attached by perforations to a plastic frame; the frame itself being attached to the waterproof plastic sheet of a conventional disposable diaper. In a second embodiment a waterproof sheet is affixed over the waterproof side of a conventional disposable diaper and sealed to it along all but one side to form a permanently attached waterproof pocket that can be turned inside out to form a bag for the used disposable diaper.

In a third embodiment, a drawstring is affixed around the periphery of the waterproof side of a conventional disposable diaper by means of a frame affixed thereto. After the diaper has been used the absorbent fiber is folded inside the waterproof side of the diaper, the drawstring is pulled tight and tied to form a bag.

For further understanding of the invention, reference should be had to the following detailed description taken in connection with the accompanying drawing, in which.

DETAILED DESCRIPTION OF THE INVENTION

Figure 1:
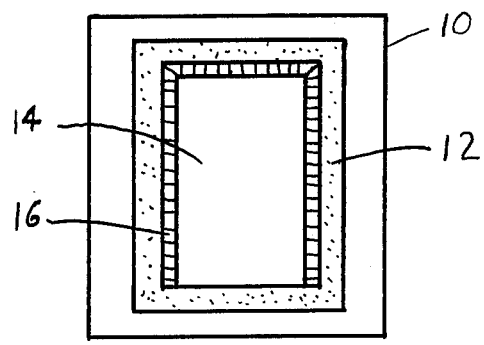
FIG. 1 is a schematic view of a combined disposable diaper and attached disposal bag.

Referring now to FIG. 1, there is represented a plastic waterproof sheet 10 that is conventionally laminated or adhered onto the mat of absorbent fibers of a conventional disposable diaper. Affixed to sheet 10 is a plastic frame 12. Preferably both sheet 10 and frame 12 are made of any plastic material having good flexibility and good handling and feeling properties such as polyethylene, polypropylene, polyvinyl chloride, polyester or polyurethane. Plastic bag 14 is affixed to frame 12 by means of perforated margin 16. Bag 14 and margin 16 are made of the same material as frame 12. Frame 12 may be affixed to sheet 10 by lamination of the frame 12 onto the sheet 10 with a hot iron press or similar method if both frame 12 and sheet 10 are made of thermoplastic material or by adhesive if both frame 12 and sheet 10 are made of infusible or thermosetting material. In this way the bag may be removed from the diaper by tearing along perforated margin 16 and the soiled diaper may be deposited inside. The bag may then be sealed by means of a string or tape (not shown) that may be tied around the bag to completely seal it. The bag itself may be coated with a suitable deodorant to combat odor.

Figure 2:
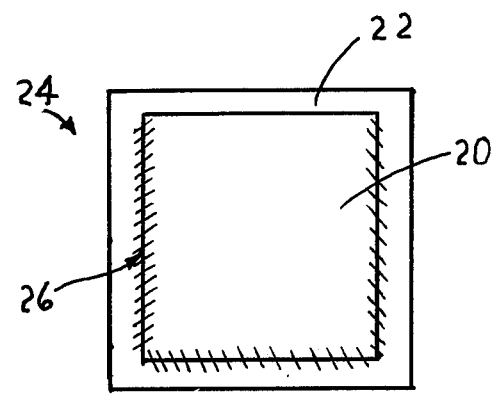
FIG. 2 is a schematic view of a combined disposable diaper and attached pocket.
Figure 2A:
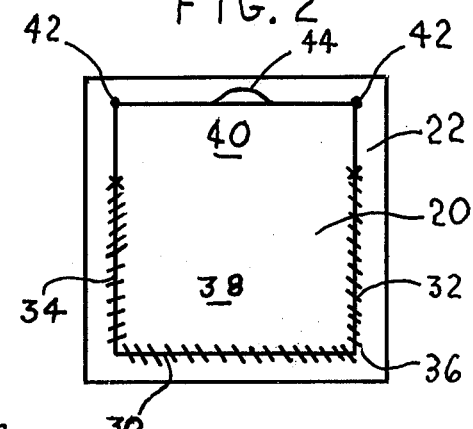
FIG. 2a is a schematic view of a modification of the device of FIG. 2.

In a second embodiment as shown schematically in FIG. 2, a single plastic sheet 20 is affixed to the waterproof side 22 of a conventional diaper 24. The sheet 20 is affixed along its periphery 26 to side 22 to form a bond 28 on all but one side to form an open-sided pocket. In this embodiment the disposable diaper has a permanently attached waterproof pocket that can be turned inside out to form a bag for the used diaper. As with the first embodiment, the sheet 20 may be affixed by lamination with a hot iron or the like if the sheet 20 and the diaper waterproof side 22 are both made of thermoplastic material or by adhesive if the sheet 20 and the side 22 are made of infusible or thermosetting material. The bag may also be sealed in the same manner as the embodiment of FIG. 1. Alternatively, as shown in FIG. 2a, sheet 20 of FIG. 2 may be affixed to side 22 along all of bottom side 30 and only a portion of sides 32,34 to from a bond 36 so that sheet 20 is divided into a pocket forming portion 38 and a flap forming portion 40. The upper corners 42 of sheet 20 may be removably attached to side 22. An adhesive tab 44 may be disposed on the flap portion. When the pocket is turned inside out to enclose the used diaper flap portion 40 may be secured over the open side of the pocket by means of tab 44 to completely seal the bag.

Figure 3:
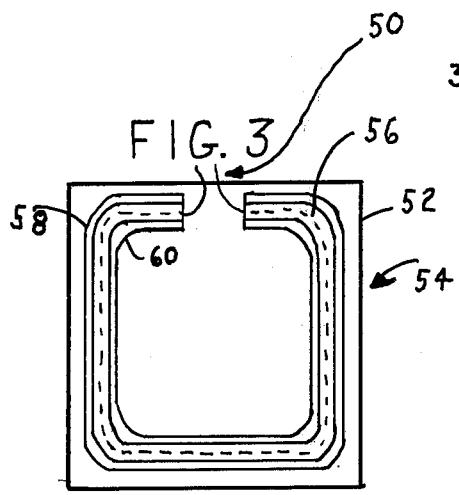
FIG. 3 is a schematic view of a disposable diaper and attached drawstring.

In a third embodiment, as shown schematically in FIG. 3, a drawstring 50 is arranged around the periphery of the waterproof side 52 of a conventional diaper 54 by means of an elongated frame 56 affixed to side 52. The longitudinal edges 58,60 of frame 56 aresecured to side 52 by continuous or intermittent lamination with a hot iron or the like if the frame 56 and side 52 are both made of a thermoplastic material. Clearance is left between the interior of the frame 56 and the side 52 to allow drawstring 50 to pass freely therebetween so that when the string is drawn it gathers side 52 into a bag to hold the absorbent fiber mat of the used diaper and any solid or liquid waste. The frame 56 may alternatively be secured to the side 52 by adhesive disposed entirely or intermittently along the longitudinal edges 58,60 of the frame 56. After the disposable diaper has been used the absorbent fiber mat is gathered inside the waterproof side 52 of diaper 54, drawstring 50 is pulled tight and tied to form a bag.

From the foregoing it can be seen that the present invention provides a simple, effective and sanitary means for disposing of a soiled disposable diaper so that it can be stored conveniently until it can be properly disposed of or left in ordinary rubbish collection containers.

While in the foregoing there has been described and shown the preferred embodiments of the invention, various modifications may become apparent to those skilled in the art to which the invention relates without departing from the scope of the invention. Accordingly it is not desired to limit the invention except as in the appended claims:

What is claimed is:

1. A combined disposable infant diaper and disposable bag comprising:
   an absorbent fiber mat having a front and back side;
   a thin, waterproof, plastic sheet having an inner and an outer surface, said inner surface of said sheet affixed to said back of said mat to form a disposable diaper;
   a means for converting said diaper into a bag comprising a narrow elongated plastic frame of substantially closed configuration juxtaposed and attached to the outer surface of said sheet adjacent the periphery thereof said frame having longitudinal edge portions and a central portion disposable therebetween;
   means of affixing said longitudinal edge portions of said frame to said sheet and leaving a passage therebetween in said central portion of said frame;
   a drawstring disposed inside the entire length of said passage and extending out of said passage so that said drawstring may be grasped and pulled tight to gather the diaper to form a waterproof bag for the used diaper and tied to seal the bag.

* * * * *